United States Patent
White et al.

(10) Patent No.: US 7,790,680 B2
(45) Date of Patent: Sep. 7, 2010

(54) STABLE PHARMACEUTICAL COMPOSITION CONTAINING FACTOR VIII

(75) Inventors: Mary White, Wrexham (GB); Paul Webb, Wrexham (GB)

(73) Assignee: Ipsen Pharma S.A.S., Paris (FR)

( * ) Notice: Subject to any disclaimer, the term of this patent is extended or adjusted under 35 U.S.C. 154(b) by 248 days.

(21) Appl. No.: 10/507,956

(22) PCT Filed: Mar. 26, 2003

(86) PCT No.: PCT/GB03/01297

§ 371 (c)(1), (2), (4) Date: Sep. 14, 2004

(87) PCT Pub. No.: WO03/080108

PCT Pub. Date: Oct. 2, 2003

(65) Prior Publication Data

US 2005/0256038 A1    Nov. 17, 2005

(30) Foreign Application Priority Data

Mar. 26, 2002  (GB) ................ 0207092.8

(51) Int. Cl.
*A61K 38/00* (2006.01)

(52) U.S. Cl. ............... 514/12; 514/2; 530/380; 530/381; 530/383

(58) Field of Classification Search .......... None
See application file for complete search history.

(56) References Cited

U.S. PATENT DOCUMENTS

| 6,024,938 | A  | * | 2/2000 | Corbo et al. ............ 424/1.69 |
| 6,586,574 | B1 | * | 7/2003 | Hansen ................... 530/384 |
| 7,576,182 | B1 | * | 8/2009 | Goddard et al. ......... 530/387.1 |
| 2004/0116345 | A1 | * | 6/2004 | Besman et al. ........... 514/12 |

FOREIGN PATENT DOCUMENTS

| JP | 64-85927   | 3/1989 |
| JP | 08-99999   | 4/1996 |
| WO | WO 01/03726 | 7/2000 |
| WO | WO 00/48635 | 8/2000 |

OTHER PUBLICATIONS

Parker et al. (J. of Thrombosis and Haemostasis, vol. 2, pp. 605-611.*
Osterberg et al, "Development . . . VIII SQ", Pharmaceutical Research, vol. 14, No. 7, 1977, pp. 892-898.

* cited by examiner

*Primary Examiner*—Hope A Robinson
(74) *Attorney, Agent, or Firm*—Hunton & Williams LLP

(57) ABSTRACT

The invention relates to a stable solid pharmaceutical composition comprising factor VIII. Such a composition is devoid of amino acids and comprises: (a) factor VIII; (b) a surfactant; (c) calcium chloride; (d) sucrose; (e) sodium chloride; (f) trisodium citrate; and (g) a buffer devoid of amino acids; and has a pH from 6 to 8 prior to lyophilization and after reconstitution in water for injection. The invention also relates to the liquid pharmaceutical composition obtainable after dilution of said stable solid pharmaceutical composition with sterile water optionally containing sodium chloride.

7 Claims, No Drawings

SEQUENCE LISTING

```
<160> NUMBER OF SEQ ID NOS: 1

<210> SEQ ID NO 1
<211> LENGTH: 1467
<212> TYPE: PRT
<213> ORGANISM: Porcine

<400> SEQUENCE: 1

Met Gln Leu Glu Leu Ser Thr Cys Val Phe Leu Cys Leu Leu Pro Leu
1               5                   10                  15

Gly Phe Ser Ala Ile Arg Arg Tyr Tyr Leu Gly Ala Val Glu Leu Ser
            20                  25                  30

Trp Asp Tyr Arg Gln Ser Glu Leu Leu Arg Glu Leu His Val Asp Thr
        35                  40                  45

Arg Phe Pro Ala Thr Ala Pro Gly Ala Leu Pro Leu Gly Pro Ser Val
    50                  55                  60

Leu Tyr Lys Lys Thr Val Phe Val Glu Phe Thr Asp Gln Leu Phe Ser
65                  70                  75                  80

Val Ala Arg Pro Arg Pro Pro Trp Met Gly Leu Leu Gly Pro Thr Ile
                85                  90                  95

Gln Ala Glu Val Tyr Asp Thr Val Val Val Thr Leu Lys Asn Met Ala
            100                 105                 110

Ser His Pro Val Ser Leu His Ala Val Gly Val Ser Phe Trp Lys Ser
        115                 120                 125

Ser Glu Gly Ala Glu Tyr Glu Asp His Thr Ser Gln Arg Glu Lys Glu
    130                 135                 140

Asp Asp Lys Val Leu Pro Gly Lys Ser Gln Thr Tyr Val Trp Gln Val
145                 150                 155                 160

Leu Lys Glu Asn Gly Pro Thr Ala Ser Asp Pro Pro Cys Leu Thr Tyr
                165                 170                 175
```

-continued

```
Ser Tyr Leu Ser His Val Asp Leu Val Lys Asp Leu Asn Ser Gly Leu
            180                 185                 190

Ile Gly Ala Leu Leu Val Cys Arg Glu Gly Ser Leu Thr Arg Glu Arg
            195                 200                 205

Thr Gln Asn Leu His Glu Phe Val Leu Leu Phe Ala Val Phe Asp Glu
            210                 215                 220

Gly Lys Ser Trp His Ser Ala Arg Asn Asp Ser Trp Thr Arg Ala Met
225                 230                 235                 240

Asp Pro Ala Pro Ala Arg Ala Gln Pro Ala Met His Thr Val Asn Gly
                245                 250                 255

Tyr Val Asn Arg Ser Leu Pro Gly Leu Ile Gly Cys His Lys Lys Ser
            260                 265                 270

Val Tyr Trp His Val Ile Gly Met Gly Thr Ser Pro Glu Val His Ser
            275                 280                 285

Ile Phe Leu Glu Gly His Thr Phe Leu Val Arg His His Arg Gln Ala
            290                 295                 300

Ser Leu Glu Ile Ser Pro Leu Thr Phe Leu Thr Ala Gln Thr Phe Leu
305                 310                 315                 320

Met Asp Leu Gly Gln Phe Leu Leu Phe Cys His Ile Ser Ser His His
                325                 330                 335

His Gly Gly Met Glu Ala His Val Arg Val Glu Ser Cys Ala Glu Glu
                340                 345                 350

Pro Gln Leu Arg Arg Lys Ala Asp Glu Glu Asp Tyr Asp Asp Asn
            355                 360                 365

Leu Tyr Asp Ser Asp Met Asp Val Val Arg Leu Asp Gly Asp Asp Val
            370                 375                 380

Ser Pro Phe Ile Gln Ile Arg Ser Val Ala Lys Lys His Pro Lys Thr
385                 390                 395                 400

Trp Val His Tyr Ile Ser Ala Glu Glu Asp Trp Asp Tyr Ala Pro
            405                 410                 415

Ala Val Pro Ser Pro Ser Asp Arg Ser Tyr Lys Ser Leu Tyr Leu Asn
            420                 425                 430

Ser Gly Pro Gln Arg Ile Gly Arg Lys Tyr Lys Lys Ala Arg Phe Val
            435                 440                 445

Ala Tyr Thr Asp Val Thr Phe Lys Thr Arg Lys Ala Ile Pro Tyr Glu
            450                 455                 460

Ser Gly Ile Leu Gly Pro Leu Leu Tyr Gly Glu Val Gly Asp Thr Leu
465                 470                 475                 480

Leu Ile Ile Phe Lys Asn Lys Ala Ser Arg Pro Tyr Asn Ile Tyr Pro
            485                 490                 495

His Gly Ile Thr Asp Val Ser Ala Leu His Pro Gly Arg Leu Leu Lys
            500                 505                 510

Gly Trp Lys His Leu Lys Asp Met Pro Ile Leu Pro Gly Glu Thr Phe
            515                 520                 525

Lys Tyr Lys Trp Thr Val Thr Val Glu Asp Gly Pro Thr Lys Ser Asp
            530                 535                 540

Pro Arg Cys Leu Thr Arg Tyr Tyr Ser Ser Ser Ile Asn Leu Glu Lys
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Met Met Ser Asp Lys Arg Asn Val
            580                 585                 590
```

-continued

Ile Leu Phe Ser Val Phe Asp Glu Asn Gln Ser Trp Tyr Leu Ala Glu
            595                 600                 605

Asn Ile Gln Arg Phe Leu Pro Asn Pro Asp Gly Leu Gln Pro Gln Asp
            610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
            645                 650                 655

Tyr Ile Leu Ser Val Gly Ala Gln Thr Asp Phe Leu Ser Val Phe Phe
            660                 665                 670

Ser Gly Tyr Thr Phe Lys His Lys Met Val Tyr Glu Asp Thr Leu Thr
            675                 680                 685

Leu Phe Pro Phe Ser Gly Glu Thr Val Phe Met Ser Met Glu Asn Pro
            690                 695                 700

Gly Leu Trp Val Leu Gly Cys His Asn Ser Asp Leu Arg Asn Arg Gly
705                 710                 715                 720

Met Thr Ala Leu Leu Lys Val Tyr Ser Cys Asp Arg Asp Ile Gly Asp
            725                 730                 735

Tyr Tyr Asp Asn Thr Tyr Glu Asp Ile Pro Gly Phe Leu Leu Ser Gly
            740                 745                 750

Lys Asn Val Ile Glu Pro Arg Ser Phe Ala Gln Asn Ser Arg Pro Pro
            755                 760                 765

Ser Ala Ser Ala Pro Lys Pro Pro Val Leu Arg Arg His Gln Arg Asp
            770                 775                 780

Ile Ser Leu Pro Thr Phe Gln Pro Glu Glu Asp Lys Met Asp Tyr Asp
785                 790                 795                 800

Asp Ile Phe Ser Thr Glu Thr Lys Gly Glu Asp Phe Asp Ile Tyr Gly
            805                 810                 815

Glu Asp Glu Asn Gln Asp Pro Arg Ser Phe Gln Lys Arg Thr Arg His
            820                 825                 830

Tyr Phe Ile Ala Ala Val Glu Gln Leu Trp Asp Tyr Gly Met Ser Glu
            835                 840                 845

Ser Pro Arg Ala Leu Arg Asn Arg Ala Gln Asn Gly Glu Val Pro Arg
850                 855                 860

Phe Lys Lys Val Val Phe Arg Glu Phe Ala Asp Gly Ser Phe Thr Gln
865                 870                 875                 880

Pro Ser Tyr Arg Gly Glu Leu Asn Lys His Leu Gly Leu Leu Gly Pro
            885                 890                 895

Tyr Ile Arg Ala Glu Val Glu Asp Asn Ile Met Val Thr Phe Lys Asn
            900                 905                 910

Gln Ala Ser Arg Pro Tyr Ser Phe Tyr Ser Ser Leu Ile Ser Tyr Pro
            915                 920                 925

Asp Asp Gln Glu Gln Gly Ala Glu Pro Arg His Asn Phe Val Gln Pro
            930                 935                 940

Asn Glu Thr Arg Thr Tyr Phe Trp Lys Val Gln His His Met Ala Pro
945                 950                 955                 960

Thr Glu Asp Glu Phe Asp Cys Lys Ala Trp Ala Tyr Phe Ser Asp Val
            965                 970                 975

Asp Leu Glu Lys Asp Val His Ser Gly Leu Ile Gly Pro Leu Leu Ile
            980                 985                 990

Cys Arg Ala Asn Thr Leu Asn Ala  Ala  His Gly Arg Gln  Val Thr Val
            995                1000                1005

-continued

```
Gln Glu Phe Ala Leu Phe Phe Thr Ile Phe Asp Glu Thr Lys Ser
    1010                1015                1020

Trp Tyr Phe Thr Glu Asn Val Glu Arg Asn Cys Arg Ala Pro Cys
    1025                1030                1035

His Leu Gln Met Glu Asp Pro Thr Leu Lys Glu Asn Tyr Arg Phe
    1040                1045                1050

His Ala Ile Asn Gly Tyr Val Met Asp Thr Leu Pro Gly Leu Val
    1055                1060                1065

Met Ala Gln Asn Gln Arg Ile Arg Trp Tyr Leu Leu Ser Met Gly
    1070                1075                1080

Ser Asn Glu Asn Ile His Ser Ile His Phe Ser Gly His Val Phe
    1085                1090                1095

Ser Val Arg Lys Lys Glu Glu Tyr Lys Met Ala Val Tyr Asn Leu
    1100                1105                1110

Tyr Pro Gly Val Phe Glu Thr Val Glu Met Leu Pro Ser Lys Val
    1115                1120                1125

Gly Ile Trp Arg Ile Glu Cys Leu Ile Gly Glu His Leu Gln Ala
    1130                1135                1140

Gly Met Ser Thr Thr Phe Leu Val Tyr Ser Lys Glu Cys Gln Ala
    1145                1150                1155

Pro Leu Gly Met Ala Ser Gly Arg Ile Arg Asp Phe Gln Ile Thr
    1160                1165                1170

Ala Ser Gly Gln Tyr Gly Gln Trp Ala Pro Lys Leu Ala Arg Leu
    1175                1180                1185

His Tyr Ser Gly Ser Ile Asn Ala Trp Ser Thr Lys Asp Pro His
    1190                1195                1200

Ser Trp Ile Lys Val Asp Leu Leu Ala Pro Met Ile Ile His Gly
    1205                1210                1215

Ile Met Thr Gln Gly Ala Arg Gln Lys Phe Ser Ser Leu Tyr Ile
    1220                1225                1230

Ser Gln Phe Ile Ile Met Tyr Ser Leu Asp Gly Arg Asn Trp Gln
    1235                1240                1245

Ser Tyr Arg Gly Asn Ser Thr Gly Thr Leu Met Val Phe Phe Gly
    1250                1255                1260

Asn Val Asp Ala Ser Gly Ile Lys His Asn Ile Phe Asn Pro Pro
    1265                1270                1275

Ile Val Ala Arg Tyr Ile Arg Leu His Pro Thr His Tyr Ser Ile
    1280                1285                1290

Arg Ser Thr Leu Arg Met Glu Leu Met Gly Cys Asp Leu Asn Ser
    1295                1300                1305

Cys Ser Met Pro Leu Gly Met Gln Asn Lys Ala Ile Ser Asp Ser
    1310                1315                1320

Gln Ile Thr Ala Ser Ser His Leu Ser Asn Ile Phe Ala Thr Trp
    1325                1330                1335

Ser Pro Ser Gln Ala Arg Leu His Leu Gln Gly Arg Thr Asn Ala
    1340                1345                1350

Trp Arg Pro Arg Val Ser Ser Ala Glu Glu Trp Leu Gln Val Asp
    1355                1360                1365

Leu Gln Lys Thr Val Lys Val Thr Gly Ile Thr Thr Gln Gly Val
    1370                1375                1380

Lys Ser Leu Leu Ser Ser Met Tyr Val Lys Glu Phe Leu Val Ser
    1385                1390                1395
```

-continued

```
Ser Ser Gln Asp Gly Arg Arg Trp Thr Leu Phe Leu Gln Asp Gly
    1400            1405            1410

His Thr Lys Val Phe Gln Gly Asn Gln Asp Ser Ser Thr Pro Val
    1415            1420            1425

Val Asn Ala Leu Asp Pro Pro Leu Phe Thr Arg Tyr Leu Arg Ile
    1430            1435            1440

His Pro Thr Ser Trp Ala Gln His Ile Ala Leu Arg Leu Glu Val
    1445            1450            1455

Leu Gly Cys Glu Ala Gln Asp Leu Tyr
    1460            1465
```

STABLE PHARMACEUTICAL COMPOSITION CONTAINING FACTOR VIII

This application is a 371 of PCT/GB03/01297 filed Mar. 26, 2003 and claims benefit under 35 USC 119 to GB 0207092.8 filed Mar. 26, 2002.

The invention relates to a new stable pharmaceutical composition containing factor VIII.

BACKGROUND OF THE INVENTION

Factor VIII is a well-known plasma protein that is essential to the blood clotting process and is therefore used in the treatment of haemophilia.

Several forms of factor VIII have been used or are intended to be used as active principles for treating haemophilia. These include human factor VIII (like the active principles of Humate® P, Monoclate® P, Immunate® or Hemofil® M), recombinant human factor VIII (like r-VIII SQ which is described in PCT patent application WO 91/09122 (the active principle of ReFacto®) or the active principles of Kogenate® or Recombinate®), porcine factor VIII (which is the active principle of the product Hyate:C® sold by Ipsen, Inc., USA) or recombinant porcine factor VIII (e.g. a modified B-domainless form of porcine factor VIII like the one disclosed in patent application WO 01/68109 and identified as "POL1212" or the protein of SEQ ID NO:38 of the same patent application).

Formulation stability has always been a problem for the pharmaceutical industry dealing with factor VIII pharmaceutical compositions.

Albumin has often been used to stabilise these formulations. However, despite its interesting stabilising effect, albumin presents the drawback of being expensive and also the risk to carry infectious species like prions. For these reasons, the pharmaceutical industry has been seeking in the recent years to replace albumin by other stabilising agents in factor VIII pharmaceutical compositions.

RELATED PRIOR ART

Several stable albumin-free pharmaceutical compositions are already known to the skilled artisan For example:

U.S. Pat. No. 5,565,427 teaches a stabilised albumin-free solution with factor VIII:C activity containing factor VIII:C, an amino acid or one of its salts or homologues and a detergent (like polysorbate 80 or Tween® 80) or an organic polymer (like polyethyleneglycol).

U.S. Pat. No. 5,605,884 relates to a stable factor VIII composition comprising factor VIII and a high ionic strength media, which is preferably consisting of an aqueous solution comprising a mixture of sodium chloride, calcium chloride and histidine as buffer ion.

U.S. Pat. Nos. 5,763,401 and 5,874,408 both disclose a stable albumin-free recombinant factor VIII composition comprising recombinant factor VIII, glycine, histidine, sucrose, sodium chloride and calcium chloride.

U.S. Pat. No. 5,962,650 teaches a stable albumin-free recombinant factor VIII composition which consists of an aqueous solution with a reduced concentration of oxygen comprising recombinant factor VIII, a calcium salt like calcium chloride and preferably an antioxidant, a non-ionic surfactant, sodium or potassium chloride, an amino acid and a mono- or disaccharide.

U.S. Pat. No. 5,972,885 relates to a pharmaceutical formulation for subcutaneous, intramuscular or intradermal administration which comprises highly concentrated (at least 1,000 IU/ml) recombinant factor VIII and, preferably, one or more elements selected from the group constituted (notably) by sodium or potassium chloride, calcium chloride, a non-ionic surfactant (e.g. a poloxamer), a mono- or disaccharide (preferably sucrose) and antioxidants (e.g. citric acid).

PCT patent application WO 89/09784 discloses a method for the production of heat-stable factor VIII concentrate which comprises gel filtration of a buffer solution containing said factor VIII and tris(hydroxymethyl)methylamine, trisodium citrate, sodium chloride, sucrose and calcium chloride followed by freeze-drying of the concentrate obtained. The factor VIII thus produced is able to withstand temperatures of up to 80° C. for up to 72 hours.

PCT patent application WO 94/07510 describes a factor VIII composition which is stabilised by a non-ionic surfactant (e.g. a poloxamer like polysorbate 80). Such a composition can also comprise one or more elements selected from the group constituted (notably) by sodium or potassium chloride, calcium chloride, an amino acid, a mono- or disaccharide such as sucrose,

BRIEF SUMMARY OF THE INVENTION

The Applicant has now unexpectedly discovered that a solid pharmaceutical composition obtainable by lyophilisation of a solution devoid of amino acids comprising the following components:

(a) factor VIII;

(b) a surfactant;

(c) calcium chloride;

(d) sucrose;

(e) sodium chloride;

(f) trisodium citrate; and (g) a buffer devoid of amino acids;

said pharmaceutical composition having a pH from 6 to 8 prior to lyophilisation and after reconstitution in water for injection, also shows stability over time.

By factor VIII is meant in the present application human factor VIII, recombinant human factor VIM, porcine factor VIM, recombinant porcine factor VIII or more generally any other recombinant factor VIII that can be used to replace them.

DETAILED DESCRIPTION OF THE INVENTION

Preferably, the factor VIII comprised in compositions according to the invention, will be chosen from porcine factor VIII or recombinant porcine factor VIII. Still more preferably, the factor VIII comprised in compositions according to the invention, will be recombinant porcine factor VIII, especially a modified B-domainless form of porcine factor VIII like the one disclosed in patent application WO 01/68109, i.e. the modified porcine factor VIII having the amino acid sequence SEQ ID NO:1 hereafter:

SEQ ID NO: 1

```
Met Gln Leu Glu Leu Ser Thr Cys Val Phe Leu Cys Leu Leu Pro Leu
  1               5                  10                  15

Gly Phe Ser Ala Ile Arg Arg Tyr Tyr Leu Gly Ala Val Glu Leu Ser
             20                  25                  30

Trp Asp Tyr Arg Gln Ser Glu Leu Leu Arg Glu Leu His Val Asp Thr
         35                  40                  45

Arg Phe Pro Ala Thr Ala Pro Gly Ala Leu Pro Leu Gly Pro Ser Val
     50                  55                  60

Leu Tyr Lys Lys Thr Val Phe Val Glu Phe Thr Asp Gln Leu Phe Ser
 65                  70                  75                  80

Val Ala Arg Pro Arg Pro Pro Trp Met Gly Leu Leu Gly Pro Thr Ile
                 85                  90                  95

Gln Ala Glu Val Tyr Asp Thr Val Val Val Thr Leu Lys Asn Met Ala
                100                 105                 110

Ser His Pro Val Ser Leu His Ala Val Gly Val Ser Phe Trp Lys Ser
             115                 120                 125

Ser Glu Gly Ala Glu Tyr Glu Asp His Thr Ser Gln Arg Glu Lys Glu
         130                 135                 140

Asp Asp Lys Val Leu Pro Gly Lys Ser Gln Thr Tyr Val Trp Gln Val
145                 150                 155                 160

Leu Lys Glu Asn Gly Pro Thr Ala Ser Asp Pro Pro Cys Leu Thr Tyr
                165                 170                 175

Ser Tyr Leu Ser His Val Asp Leu Val Lys Asp Leu Asn Ser Gly Leu
             180                 185                 190

Ile Gly Ala Leu Leu Val Cys Arg Glu Gly Ser Leu Thr Arg Glu Arg
         195                 200                 205

Thr Gln Asn Leu His Glu Phe Val Leu Leu Phe Ala Val Phe Asp Glu
     210                 215                 220

Gly Lys Ser Trp His Ser Ala Arg Asn Asp Ser Trp Thr Arg Ala Met
225                 230                 235                 240

Asp Pro Ala Pro Ala Arg Ala Gln Pro Ala Met His Thr Val Asn Gly
                245                 250                 255

Tyr Val Asn Arg Ser Leu Pro Gly Leu Ile Gly Cys His Lys Lys Ser
             260                 265                 270

Val Tyr Trp His Val Ile Gly Met Gly Thr Ser Pro Glu Val His Ser
         275                 280                 285

Ile Phe Leu Glu Gly His Thr Phe Leu Val Arg His His Arg Gln Ala
     290                 295                 300

Ser Leu Glu Ile Ser Pro Leu Thr Phe Leu Thr Ala Gln Thr Phe Leu
305                 310                 315                 320

Met Asp Leu Gly Gln Phe Leu Leu Phe Cys His Ile Ser Ser His His
                325                 330                 335

His Gly Gly Met Glu Ala His Val Arg Val Glu Ser Cys Ala Glu Glu
             340                 345                 350

Pro Gln Leu Arg Arg Lys Ala Asp Glu Glu Glu Asp Tyr Asp Asp Asn
         355                 360                 365

Leu Tyr Asp Ser Asp Met Asp Val Val Arg Leu Asp Gly Asp Asp Val
     370                 375                 380

Ser Pro Phe Ile Gln Ile Arg Ser Val Ala Lys Lys His Pro Lys Thr
385                 390                 395                 400

Trp Val His Tyr Ile Ser Ala Glu Glu Glu Asp Trp Asp Tyr Ala Pro
                405                 410                 415
```

-continued

```
Ala Val Pro Ser Pro Ser Asp Arg Ser Tyr Lys Ser Leu Tyr Leu Asn
                420                 425                 430

Ser Gly Pro Gln Arg Ile Gly Arg Lys Tyr Lys Lys Ala Arg Phe Val
            435                 440                 445

Ala Tyr Thr Asp Val Thr Phe Lys Thr Arg Lys Ala Ile Pro Tyr Glu
        450                 455                 460

Ser Gly Ile Leu Gly Pro Leu Leu Tyr Gly Glu Val Gly Asp Thr Leu
465                 470                 475                 480

Leu Ile Ile Phe Lys Asn Lys Ala Ser Arg Pro Tyr Asn Ile Tyr Pro
                485                 490                 495

His Gly Ile Thr Asp Val Ser Ala Leu His Pro Gly Arg Leu Leu Lys
            500                 505                 510

Gly Trp Lys His Leu Lys Asp Met Pro Ile Leu Pro Gly Glu Thr Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Ile Asn Leu Glu Lys
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Met Met Ser Asp Lys Arg Asn Val
            580                 585                 590

Ile Leu Phe Ser Val Phe Asp Glu Asn Gln Ser Trp Tyr Leu Ala Glu
        595                 600                 605

Asn Ile Gln Arg Phe Leu Pro Asn Pro Asp Gly Leu Gln Pro Gln Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Val Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Val Leu Gly Cys His Asn Ser Asp Leu Arg Asn Arg Gly
705                 710                 715                 720

Met Thr Ala Leu Leu Lys Val Tyr Ser Cys Asp Arg Asp Ile Gly Asp
                725                 730                 735

Tyr Tyr Asp Asn Thr Tyr Glu Asp Ile Pro Gly Phe Leu Leu Ser Gly
            740                 745                 750

Lys Asn Val Ile Glu Pro Arg Ser Phe Ala Gln Asn Ser Arg Pro Pro
        755                 760                 765

Ser Ala Ser Ala Pro Lys Pro Pro Val Leu Arg Arg His Gln Arg Asp
    770                 775                 780

Ile Ser Leu Pro Thr Phe Gln Pro Glu Glu Asp Lys Met Asp Tyr Asp
785                 790                 795                 800

Asp Ile Phe Ser Thr Glu Thr Lys Gly Glu Asp Phe Asp Ile Tyr Gly
                805                 810                 815

Glu Asp Glu Asn Gln Asp Pro Arg Ser Phe Gln Lys Arg Thr Arg His
            820                 825                 830
```

-continued

```
Tyr Phe Ile Ala Ala Val Glu Gln Leu Trp Asp Tyr Gly Met Ser Glu
        835                 840                 845

Ser Pro Arg Ala Leu Arg Asn Arg Ala Gln Asn Gly Glu Val Pro Arg
    850                 855                 860

Phe Lys Lys Val Val Phe Arg Glu Phe Ala Asp Gly Ser Phe Thr Gln
865                 870                 875                 880

Pro Ser Tyr Arg Gly Glu Leu Asn Lys His Leu Gly Leu Leu Gly Pro
                885                 890                 895

Tyr Ile Arg Ala Glu Val Glu Asp Asn Ile Met Val Thr Phe Lys Asn
            900                 905                 910

Gln Ala Ser Arg Pro Tyr Ser Phe Tyr Ser Ser Leu Ile Ser Tyr Pro
        915                 920                 925

Asp Asp Gln Glu Gln Gly Ala Glu Pro Arg His Asn Phe Val Gln Pro
    930                 935                 940

Asn Glu Thr Arg Thr Tyr Phe Trp Lys Val Gln His His Met Ala Pro
945                 950                 955                 960

Thr Glu Asp Glu Phe Asp Cys Lys Ala Trp Ala Tyr Phe Ser Asp Val
                965                 970                 975

Asp Leu Glu Lys Asp Val His Ser Gly Leu Ile Gly Pro Leu Leu Ile
            980                 985                 990

Cys Arg Ala Asn Thr Leu Asn Ala Ala His Gly Arg Gln Val Thr Val
        995                 1000                1005

Gln Glu Phe Ala Leu Phe Phe Thr Ile Phe Asp Glu Thr Lys Ser Trp
    1010                1015                1020

Tyr Phe Thr Glu Asn Val Glu Arg Asn Cys Arg Ala Pro Cys His Leu
1025                1030                1035                1040

Gln Met Glu Asp Pro Thr Leu Lys Glu Asn Tyr Arg Phe His Ala Ile
                1045                1050                1055

Asn Gly Tyr Val Met Asp Thr Leu Pro Gly Leu Val Met Ala Gln Asn
            1060                1065                1070

Gln Arg Ile Arg Trp Tyr Leu Leu Ser Met Gly Ser Asn Glu Asn Ile
        1075                1080                1085

His Ser Ile His Phe Ser Gly His Val Phe Ser Val Arg Lys Lys Glu
    1090                1095                1100

Glu Tyr Lys Met Ala Val Tyr Asn Leu Tyr Pro Gly Val Phe Glu Thr
1105                1110                1115                1120

Val Glu Met Leu Pro Ser Lys Val Gly Ile Trp Arg Ile Glu Cys Leu
                1125                1130                1135

Ile Gly Glu His Leu Gln Ala Gly Met Ser Thr Thr Phe Leu Val Tyr
            1140                1145                1150

Ser Lys Glu Cys Gln Ala Pro Leu Gly Met Ala Ser Gly Arg Ile Arg
        1155                1160                1165

Asp Phe Gln Ile Thr Ala Ser Gly Gln Tyr Gly Gln Trp Ala Pro Lys
    1170                1175                1180

Leu Ala Arg Leu His Tyr Ser Gly Ser Ile Asn Ala Trp Ser Thr Lys
1185                1190                1195                1200

Asp Pro His Ser Trp Ile Lys Val Asp Leu Leu Ala Pro Met Ile Ile
                1205                1210                1215

His Gly Ile Met Thr Gln Gly Ala Arg Gln Lys Phe Ser Ser Leu Tyr
            1220                1225                1230

Ile Ser Gln Phe Ile Ile Met Tyr Ser Leu Asp Gly Arg Asn Trp Gln
        1235                1240                1245
```

-continued

```
Ser Tyr Arg Gly Asn Ser Thr Gly Thr Leu Met Val Phe Phe Gly Asn
    1250                1255                1260

Val Asp Ala Ser Gly Ile Lys His Asn Ile Phe Asn Pro Pro Ile Val
1265                1270                1275                1280

Ala Arg Tyr Ile Arg Leu His Pro Thr His Tyr Ser Ile Arg Ser Thr
                1285                1290                1295

Leu Arg Met Glu Leu Met Gly Cys Asp Leu Asn Ser Cys Ser Met Pro
            1300                1305                1310

Leu Gly Met Gln Asn Lys Ala Ile Ser Asp Ser Gln Ile Thr Ala Ser
        1315                1320                1325

Ser His Leu Ser Asn Ile Phe Ala Thr Trp Ser Pro Ser Gln Ala Arg
    1330                1335                1340

Leu His Leu Gln Gly Arg Thr Asn Ala Trp Arg Pro Arg Val Ser Ser
1345                1350                1355                1360

Ala Glu Glu Trp Leu Gln Val Asp Leu Gln Lys Thr Val Lys Val Thr
                1365                1370                1375

Gly Ile Thr Thr Gln Gly Val Lys Ser Leu Leu Ser Ser Met Tyr Val
            1380                1385                1390

Lys Glu Phe Leu Val Ser Ser Ser Gln Asp Gly Arg Arg Trp Thr Leu
        1395                1400                1405

Phe Leu Gln Asp Gly His Thr Lys Val Phe Gln Gly Asn Gln Asp Ser
    1410                1415                1420

Ser Thr Pro Val Val Asn Ala Leu Asp Pro Pro Leu Phe Thr Arg Tyr
1425                1430                1435                1440

Leu Arg Ile His Pro Thr Ser Trp Ala Gln His Ile Ala Leu Arg Leu
                1445                1450                1455

Glu Val Leu Gly Cys Glu Ala Gln Asp Leu Tyr
            1460                1465
```

Preferably, the surfactant will be a non-ionic surfactant. Non-ionic surfactants include notably polysorbates and block copolymers like poloxamers (i.e. copolymers of polyethylene and propylene glycol). According to a preferred variant of the invention, the surfactant will be a polysorbate. More preferably, a polysorbate included in a composition according to the instant invention will have a mean polymerisation degree of from 20 to 100 monomer units (preferably about 80), and may for example be polysorbate 80. Preferably also, the polysorbate should be vegetable-derived.

Preferably, the buffer devoid of amino acids will be tris (hydroxymethyl)methylamine (hereafter abridged "tris").

Preferably also, the pH of the pharmaceutical composition prior to lyophilisation and after reconstitution in water for injection will be from 6.5 to 7.5, and more preferably about 7.0.

Preferably, a solid composition according to the invention will be such that it may be obtained by lyophilisation of a solution devoid of amino acids that comprises:
(a) a concentration of factor VIII ranging from 50 to 10,000 international units/ml for human or recombinant human factor VIII or from 50 to 10,000 porcine units/ml for porcine or recombinant porcine factor VIII;
(b) a concentration of surfactant ranging from above critical micellar concentration to 1% v/v;
(c) a concentration of calcium chloride ranging from 0.5 to 10 mM;
(d) a concentration of sucrose ranging from 5 to 50 mM;
(e) a concentration of sodium chloride ranging from 0.15 to 0.5 M;
(f) a concentration of trisodium citrate ranging from 1 to 50 mM; and
(g) a concentration of buffer devoid of amino acids ranging from 1 to 50 mM.

For evaluating the activity in terms of international factor VIII units, the product to be tested is assayed against a Concentrate Standard, such as the United Kingdom standard NIBSC 95/608 (NIBSC for National Institute of Biological Standards and Control).

By porcine unit of factor VIII is meant the United Kingdom national standard unit held by United Kingdom's NIBSC. For evaluating the activity in terms of porcine factor VIII units, the product to be tested is assayed against the UK national porcine standard NIBSC 86/514. Concerning recombinant porcine factor VIII, it should be understood that 1 unit of activity for recombinant porcine factor VIII is equivalent to 1 unit of activity for porcine factor VIII.

More preferably, a solid composition according to the invention will be such that it may be obtained by lyophilisation of a solution devoid of amino acids that comprises at least one of the following characteristics:
  a concentration of factor VIII ranging from 100 to 5,000 international units/ml for human or recombinant human factor VIII or from 100 to 5,000 porcine units/ml for porcine or recombinant porcine factor VIII;
  a concentration of surfactant ranging from 0.002% to 0.04% v/v;

a concentration of calcium chloride ranging from 1 to 5 mM;

a concentration of sucrose ranging from 5 to 25 mM;

a concentration of sodium chloride ranging from 0.2 to 0.4 M;

a concentration of trisodium citrate ranging from 1 to 20 mM; or a concentration of buffer devoid of amino acids ranging from 1 to 20 mM.

Even more preferably, a solid composition according to the invention will be such that it may be obtained by lyophilisation of a solution devoid of amino acids that comprises at least one of the following characteristics:

a concentration of factor VIII ranging from 200 to 2,000 international units/ml (and notably about 1,000 international units/ml) for human or recombinant human factor VIII or from 200 to 2,000 porcine units/ml (and notably about 1,000 porcine units/ml) for porcine or recombinant porcine factor VIII;

a concentration of surfactant ranging from about 0.002% to 0.02% v/v (and notably about 0.01% v/v);

a concentration of calcium chloride ranging from 1 to 3 mM (and notably about 2 mM);

a concentration of sucrose ranging from 5 to 15 mM (and notably about 11.7 mM);

a concentration of sodium chloride ranging from 0.25 to 0.35 M (and notably about 0.3 M);

a concentration of trisodium citrate ranging from 1 to 20 mM (and notably about 10 mM); or a concentration of buffer devoid of amino acids ranging from 5 to 15 mM (and notably about 10 mM).

The solid factor VIII compositions according to the invention may be prepared by lyophilising a solution comprising the appropriate quantities of the components identified above as (a), (b), (c), (d), (e), (f) and (g) according to standard manufacturing procedures (sterile conditions, etc.).

Stability of the composition over a certain period may be determined, for example, by the method described hereunder in the part entitled "Analytical methods", or by any other method found appropriate by the skilled artisan.

A composition according to the invention is considered stable during a certain period of time if 70% to 130% (and preferably 80% to 120%) of the initial factor VIII activity, as evaluated using the method disclosed the part entitled "Analytical methods" hereafter, is maintained over said period of time.

Preferably, the solid compositions of this invention will be stable for at least 6 or 12 months when kept at a temperature of 2 to 8° C. More preferably, they will be stable for at least 6 or 12 months when kept at a temperature of 30 to 32° C.

The solid factor VIII compositions according to the invention may be diluted with sterile water optionally containing sodium chloride, and the resulting liquid pharmaceutical composition may then be directly injected into a patient in need thereof. The resulting liquid pharmaceutical composition, as well as liquid pharmaceutical compositions obtainable by dilution of solid factor VIII compositions according to the invention with sterile water optionally containing sodium chloride, are also part of this invention.

Methods of treatment of haemophilia comprising the administration of a liquid composition according to the invention to a patient in need thereof are also within the scope of this invention. The administration mode contemplated for liquid compositions according to the instant invention will preferably be intravenous administration. The dose of composition according to the instant invention which is to be administered will be determined by the treating physician or veterinarian, taking into account the severity of the disease for each patient.

The term "about" refers to an interval around the considered value. As used in this patent application, "about X" means an interval from X minus 10% of X to X plus 10% of X, and preferably an interval from X minus 5% of X to X plus 5% of X.

Unless they are defined differently, all the technical and scientific terms used here have the same meaning as that usually understood by an ordinary specialist in the field to which this invention belongs. Similarly, all publications, patent applications, all patents and all other references mentioned here are incorporated by way of reference.

The following examples are presented to illustrate the above and must in no case be considered as a limit to the scope of the invention.

EXAMPLES

Example 1

A solution in 0.5 ml sterile water containing the following components is prepared:

| | |
|---|---|
| Modified porcine factor VIII of sequence SEQ ID NO: 1 | 800 porcine units/ml |
| Vegetable derived polysorbate 80 | 0.01% v/v |
| Calcium chloride | 2 mM |
| Sucrose | 11.7 mM |
| Sodium chloride | 0.3 M |
| Tri sodium citrate | 10 mM |
| Tris buffer | 10 mM |
| pH | 7.0 |

The mixture is lyophilised in a sterilised vial which is then sealed. The solid composition obtained has been tested and shown to be stable at a temperature of 2 to 8° C. for at least 18 months and at 30 to 32° C. for at least six months when tested by factor VIII activity. There was no indication of high molecular weight component formation as assessed by Size Exclusion HPLC (SEC HPLC) or fragments as assessed by SDS PAGE.

The lyophilised mixture obtained would typically be reconstituted with 1.0 ml sterile water before injection into a patient.

Example 2

A solution in 1.0 ml sterile water containing the following components is prepared:

| | |
|---|---|
| Modified porcine factor VIII of sequence SEQ ID NO: 1 | 400 porcine units/ml |
| Vegetable derived polysorbate 80 | 0.002% v/v |
| Calcium chloride | 2 mM |
| Sucrose | 11.7 mM |
| Sodium chloride | 0.3 M |
| Tri sodium citrate | 10 mM |
| Tris buffer | 10 mM |
| pH | 7.0 |

The mixture is lyophilised in a sterilised vial which is then sealed.

The lyophilised mixture obtained would typically be reconstituted with 2.0 ml sterile water before injection into a patient.

Example 3

A solution in 0.5 ml sterile water containing the following components is prepared:

| | |
|---|---|
| Plasma-derived porcine factor VIII | 100 porcine units/ml |
| Vegetable derived polysorbate 80 | 0.01% v/v |
| Calcium chloride | 2 mM |
| Sucrose | 11.7 mM |
| Sodium chloride | 0.3 M |
| Tri sodium citrate | 10 mM |
| Tris buffer | 10 mM |
| pH | 7.0 |

The mixture is lyophilised in a sterilised vial which is then sealed.

The lyophilised mixture obtained would typically be reconstituted with 1.0 ml sterile water before injection into a patient.

Analytical Methods

Chromogenic Assay

The factor VIII activity is determined by a modified chromogenic assay (Technochrom FVIII:C Reagent Kit, Technoclone). The generation of activated factor X by factor IX is stimulated by factor VIII which acts as a cofactor in the reaction. The release of p-nitroaniline from the chromogenic substrate is catalysed by activated factor X. The amount of p-nitroaniline which is released is measured photometrically at 405 nm and the assay gives a linear correlation between the amount of p-nitroaniline generated and the FVIII content.

SEC HPLC

Soluble high molecular weight components and fragments were determined by gel filtration performed on a HPLC instrument using a TosoHaas TSK G3000 SVXL, 0.78×30 cm pre-packed column with a fluorescence detector (Waters LC Module 1 plus). Excitation wavelength 280 nm and emission wavelength 340 nm. Evaluation of the results were performed by integration of the peak areas.

SDS PAGE Assay

SDS PAGE (polyacylamide gel electrophoresis using a flatbed electrophoresis system (Multiphor II LKB) and pre cast 7.5% gels (EXCELGEL SDS, Pharmacia) was used to determine any breakdown products of the FVIII molecule. Protein bands were visualised by Coomassie blue staining.

Stability Assay

Stability can be assayed by performing the above described assays at different times on a sample of the same composition held at the temperature chosen (which may be around +4° C. or +31° C.). Once its factor VIII activity will have dropped of more than 30%, the composition will be considered to have lost its stability.

The invention claimed is:

1. A solid pharmaceutical composition comprising a lyophilized solution devoid of amino acids, wherein said solution comprises:
   (a) mature recombinant porcine factor VIII, wherein said mature recombinant porcine factor VIII extends from amino acid residue 20 to amino acid residue 1467 of;
   (b) a surfactant;
   (c) calcium chloride;
   (d) sucrose;
   (e) sodium chloride;
   (f) trisodium citrate; and
   (g) a buffer devoid of amino acids;
   wherein said solution has a pH from 6 to 8 prior to lyophilization and wherein said solid pharmaceutical composition results in a solution having a pH from 6 to 8 after reconstitution in water for injection.

2. The solid pharmaceutical composition of claim 1 wherein the surfactant is polysorbate.

3. The solid pharmaceutical composition of claim 2 wherein the surfactant is a polysorbate 80.

4. The solid pharmaceutical composition of claim 1 wherein the buffer devoid of amino acids is TRIS(hydroxymethyl)methylamine.

5. The solid pharmaceutical composition of claim 1 wherein the solution devoid of amino acids has a pH from 6.5 to 7.5 prior to lyophilization and wherein said solid pharmaceutical composition results in a solution having a pH from 6.5 to 7.5 after reconstitution in water for injection.

6. The solid pharmaceutical composition of claim 1, wherein the solution devoid of amino acids comprises:
   (a) a concentration of factor VIII from 50 to 10,000 porcine units/ml for mature recombinant porcine factor VIII;
   (b) a concentration of surfactant from above critical micellar concentration to 1% v/v;
   (c) a concentration of calcium chloride from 0.5 to 10 mM;
   (d) a concentration of sucrose from 5 to 50 mM;
   (e) a concentration of sodium chloride from 0.15 to 0.5 M;
   (f) a concentration of trisodium citrate from 1 to 50 mM; and
   (g) a concentration of a buffer devoid of amino acids from 1 to 50 mM.

7. The liquid pharmaceutical composition obtainable after dilution of a solid pharmaceutical composition of claim 1 with sterile water optionally containing sodium chloride.

* * * * *